United States Patent
Adams et al.

(10) Patent No.: US 10,254,219 B1
(45) Date of Patent: Apr. 9, 2019

(54) SYSTEM AND METHOD FOR VISUALLY ALIGNING TERAHERTZ LIGHT BEAM

(71) Applicant: Ford Motor Company, Dearborn, MI (US)

(72) Inventors: Scott Adams, Milan, MI (US); Tony Misovski, Oxford, MI (US); Mark Edward Nichols, Saline, MI (US); Marina Menendez Baker, Southgate, MI (US)

(73) Assignee: Ford Motor Company, Dearborn, MI (US)

( * ) Notice: Subject to any disclaimer, the term of this patent is extended or adjusted under 35 U.S.C. 154(b) by 0 days.

(21) Appl. No.: 15/795,297

(22) Filed: Oct. 27, 2017

(51) Int. Cl.
  *G01N 21/3581* (2014.01)
  *H01L 27/146* (2006.01)
  *G01J 3/10* (2006.01)
  *G01J 3/42* (2006.01)

(52) U.S. Cl.
  CPC ............ *G01N 21/3581* (2013.01); *G01J 3/10* (2013.01); *G01J 3/42* (2013.01); *H01L 27/146* (2013.01)

(58) Field of Classification Search
  CPC .......... G01J 3/42; G01J 3/10; G01N 21/3581; H01L 27/146
  See application file for complete search history.

(56) References Cited

U.S. PATENT DOCUMENTS

| | | | |
|---|---|---|---|
| 6,631,000 B1 | 10/2003 | Schwarz | |
| 8,001,830 B2 | 8/2011 | Dazzi et al. | |
| 8,233,049 B2 | 7/2012 | Kasai et al. | |
| 8,946,632 B2 | 2/2015 | Federici et al. | |
| 9,322,712 B2 | 4/2016 | Neshat et al. | |
| 2011/0168891 A1 | 7/2011 | van der Weide et al. | |
| 2013/0204577 A1* | 8/2013 | Savard | G01B 11/0625 702/172 |
| 2016/0245744 A1 | 8/2016 | Itsuji | |
| 2017/0050208 A1 | 2/2017 | Nichols et al. | |
| 2017/0059409 A1 | 3/2017 | Eom | |

FOREIGN PATENT DOCUMENTS

DE  102008054579  6/2010

OTHER PUBLICATIONS

Yardimci, Nezih Tolga et al., High Sensitivity Terahertz Detection Through Large-Area Plasmonic Nano-Antenna Arrays, Scientific Reports 7, 42667; doi:10.1038/srep42667, Feb. 2017. Available at URL www.nature.com/scientificreports.

* cited by examiner

*Primary Examiner* — David P Porta
*Assistant Examiner* — Faye Boosalis
(74) *Attorney, Agent, or Firm* — Burris Law, PLLC (57) ABSTRACT

A system for measuring a coating thickness on a target surface includes a terahertz spectroscopy device and a reference image projector. The terahertz spectroscopy device includes a radiation head that is operable to project a terahertz radiation beam onto the target surface and receive a reflected beam. The reference image projector includes a visible light device and is operable to project a reference image using the visible light device onto the target surface. A visual characteristic of the reference image indicates at least one of distance, rotational alignment, and angular alignment of the radiation head relative to the target surface.

20 Claims, 5 Drawing Sheets

SYSTEM AND METHOD FOR VISUALLY ALIGNING TERAHERTZ LIGHT BEAM

FIELD

The present invention relates to a system and method for aligning a terahertz radiation beam for measuring thickness of multiple layers on a surface.

BACKGROUND

The statements in this section merely provide background information related to the present disclosure and may not constitute prior art.

The exterior of a vehicle generally includes multiple layers of paint and/or other coatings, such as electrocoat, primer, basecoat, and clear coat. Each layer has a minimum film build designed to inhibit the degradation and potential delamination of the exterior due to, for example, UV and visible light, and to provide the appropriate appearance/color to the vehicle, and to protect the substrate from environmental damage.

While various paint thickness measurement techniques are available for measuring a single layer of paint, there are a limited number of non-destructive measurement techniques for measuring multiple layers. One such measurement technique utilizes ultrasound technology in which an ultrasonic transducer is placed on the exterior surface, and sends an ultrasonic signal through the exterior surface. A liquid couplant, usually water, is used to transmit the signal into the coating material. The ultrasonic signal generates an echo at the layer interfaces, and the thickness is determined based on the time difference between the successive echoes. Sound velocity values vary among the different coatings, so calibration is performed on all layers in addition to the various basecoat colors.

While the ultrasound technique is effective, there are some issues with this technique. For example, the transducer size and the tool used for the transducer may not allow measurement of certain vehicle surfaces, such as a windshield flange, and thus, a separate procedure is usually employed to obtain data of those areas. Another issue is that the transducer requires a large (e.g., 10 mm diameter) flat area in order to generate adequate waveforms. This requires selecting points on a vehicle based on their flatness rather than being able to select locations on the vehicle that are of interest but may not be flat. Furthermore, the transducer physically contacts the vehicle. Although damage from the transducer may not occur, the water left on the body affects other quality control measures, such as a dirt detection quality check.

Another technique for measuring a multi-layer surface includes the use of a radiation beam having a terahertz (THz) frequency. Using a THz light source to generate a THz radiation beam, a THz head is positioned at a designated offset and is normal to a target surface of the vehicle before the measurement is performed. For example, the radiation head can be attached to a robot or some other piece of automation to allow it to track the contour surfaces and the complex geometries. The THz radiation beam is emitted from the Thz radiation head and reflects off the vehicle due to a change in refractive index. The time difference between the emission and reflection is used to calculate the thickness. The THz signal reflects off of the coating interfaces, due to a change in refractive index, and the time difference of the reflection is used to calculate the thickness.

Since the THz head is fairly compact and does not contact the surface of the vehicle, it can be used to measure places not measurable by an ultrasonic transducer, such as the windshield flange. The THz radiation beam is typically 1 mm in diameter which enables measurement of multiple regions that have a flat section of that size.

However, for an optimal measurement, the THz radiation head should be aligned normal to a target surface of the vehicle so that the emitter of the radiation head aligns with the detector of the radiation head. When the emitter and detector are aligned, the amplitude of the reflected radiation signal is usually at the maximum value. If the radiation head is not normal to the surface, the reflected radiation signal may not align with the detectors, which results in a lower peak amplitude. This loss in signal may affect the results of the thickness measurement. Misalignment during the calibration procedure would also result in an incorrect calibration file and bad data. These and other issues are addressed by the teachings of the present disclosure.

SUMMARY

This section provides a general summary of the disclosure, and is not a comprehensive disclosure of its full scope or all of its features.

In one form, the present disclosure is directed towards a system for measuring the thickness of a coating on a target surface. The system includes a terahertz spectroscopy device and a reference image projector. The terahertz spectroscopy device includes a radiation head that is operable to project a terahertz radiation beam onto a target surface and receive a reflected beam. The reference image projector includes a visible light device and operable to project a reference image using a visible light source onto the target surface. A visual characteristic of the reference image indicates at least one of distance, rotational alignment, and angular alignment of the radiation head relative to the target surface.

In another form, the terahertz spectroscopy device includes a terahertz light source that is operable to generate the terahertz radiation beam, and the radiation head that includes an emitter to emit the terahertz radiation beam and a detector for receiving the reflected beams.

In yet another form, the visible light device is positioned with the radiation head.

In one form, the system further includes a controller configured to control the position and orientation of the radiation head with respect to the target surface based on the visual characteristic of the reference image.

In another form, the reference image comprises at least two patterns that are superimposed with each other. Each pattern has a visual characteristic that is dependent on the position of the radiation head with respect to the target surface, and is independent of the other patterns.

In yet another form, one pattern of the at least two patterns is a plurality of dots arranged in a matrix form and another pattern of the at least two patterns is multiple rings having different diameters and concentrically positioned with one another.

In one form, the at least two patterns are different geometric shapes that are superimposed with each other.

In another form, the visual characteristic of the reference image includes at least one of size, deformation, and rotational position.

In one form, the present disclosure is directed toward a method for aligning a terahertz radiation head of a spectroscopy device with a target surface. The method includes: projecting, by a visible light source, a reference image onto the target surface; analyzing a visual characteristic of the reference image to determine the alignment of the terahertz radiation head with respect to the target surface; and aligning the terahertz radiation head with the target surface such that the visual characteristic of the reference image is within a calibrated visual characteristic. A terahertz radiation beam emitted from the terahertz radiation head is surrounded by the reference image, and the visual characteristic of the reference image is indicative of at least one of distance, angle, and rotational orientation of the terahertz radiation head.

In another form, the calibrated visual characteristic is representative of the reference image when an alignment of the terahertz radiation head with respect to the target surface is optimal for receiving a reflected terahertz radiation beam from the target surface.

In yet another form, the projecting the reference image further includes projecting at least two patterns that are superimposed with each other on the target surface to form the reference image.

In one form, the present disclosure is directed toward an alignment method for a terahertz radiation head of a spectroscopy device with a target surface of a vehicle. The method includes: projecting an image onto the target surface using a visible light source; and aligning the terahertz radiation head with the target surface until a visual characteristic of the image meets a calibrated characteristic. The calibrated characteristic is representative of the image when the terahertz radiation head is at a calibrated position.

In another form, the projecting the image further includes projecting two patterns that are superimposed with each other on the target surface to form the reference image. Each pattern has a visual characteristic that is dependent on the position of the terahertz radiation head with respect to the target surface, and is independent of the other pattern.

In yet another form, the visual characteristic of the image is indicative of at least one of distance, angle, and rotational orientation of the terahertz radiation head.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

A terahertz radiation beam is not visible to the human eye, and thus may be difficult to align the radiation head, such that is its perpendicular to a target surface. While some systems include a single visible laser beam aligned with the radiation head to aid in the alignment of the radiation head, the laser beam does not provide the operator with an indication of distance from the radiation head nor does it provide an indication of rotation about the radiation head.

The present disclosure is directed toward a terahertz sensory system that includes a reference image projector for projecting a reference image onto a target surface of the vehicle that provides a visual tool for aligning a radiation head of the system with the target surface. As described further herein, a visual characteristic of the reference image is used to indicate, for example, distance and rotational alignment of the radiation head relative to the target surface.

Figure 1:
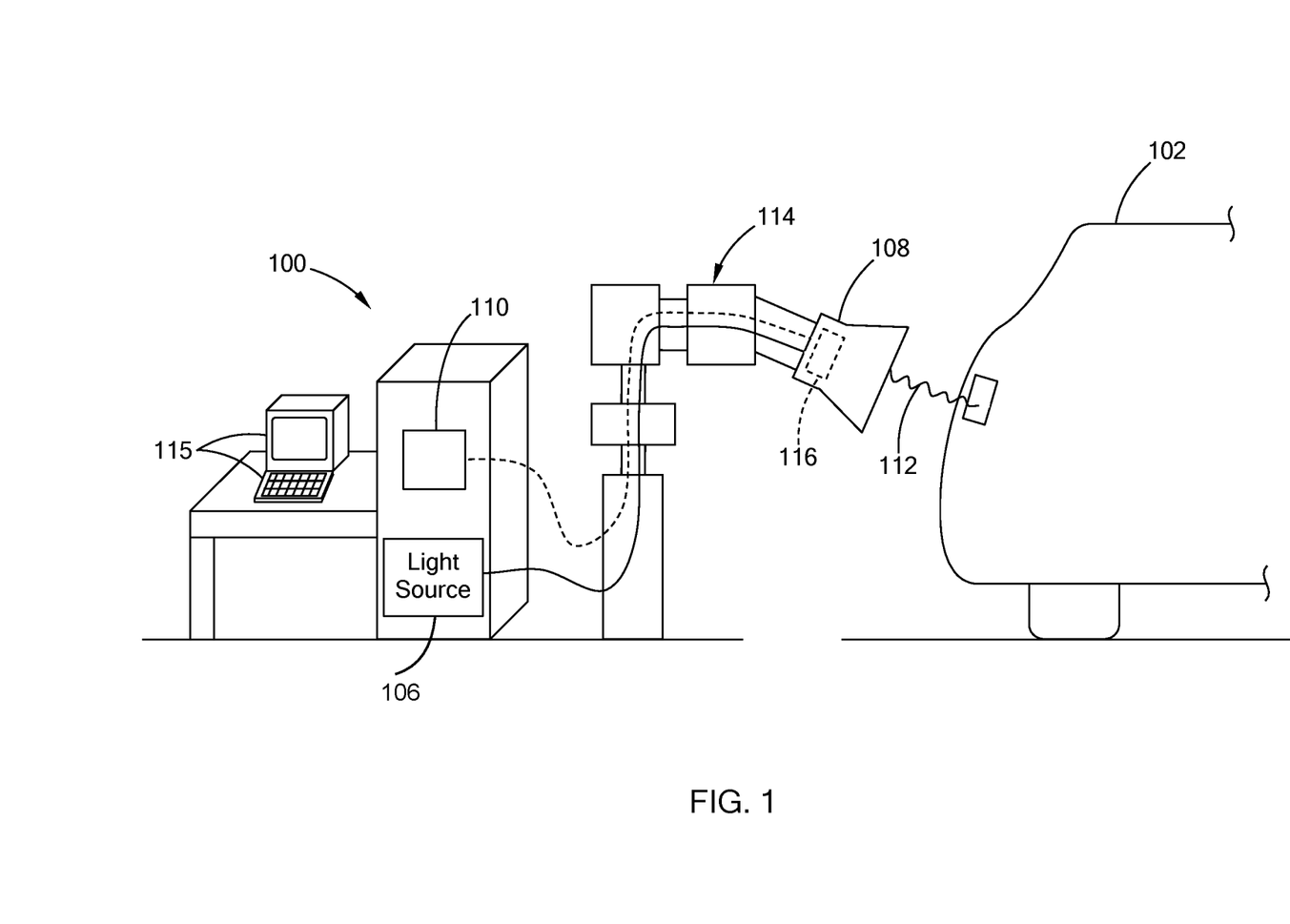
FIG. 1 a schematic of a terahertz (THz) sensory system having a reference image projector in accordance with the teachings of the present disclosure.

Referring to FIG. 1, a terahertz (THz) sensory system 100 for measuring the thickness of one or more paint layers on a vehicle body 102. The system 100 includes a light source 106, a radiation head 108 coupled to the light source 106, and a controller 110. The light source 106 is operable to generate a radiation beam 112 within the THz frequency range. Accordingly, the radiation beam 112 is in a region of the electromagnetic spectrum that includes microwaves and infrared light wave. The radiation beam 112 can penetrate a wide variety of materials and travel in a line of sight.

Figure 2:
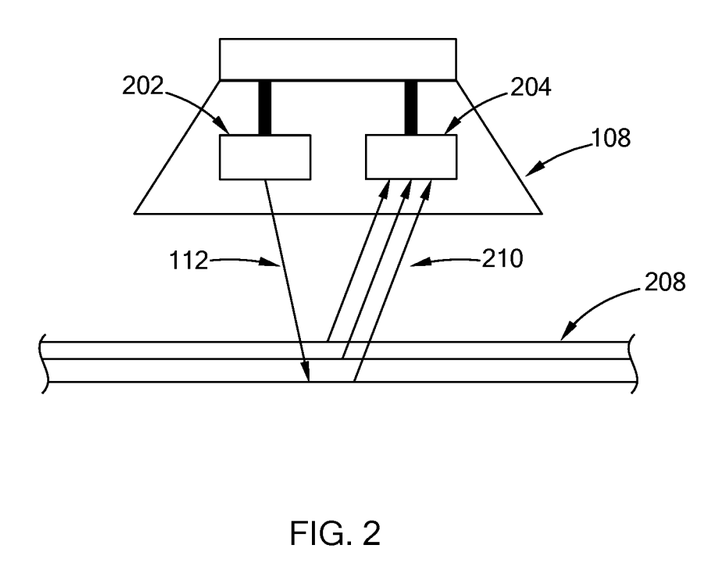
FIG. 2 a schematic of a radiation head of the system of FIG. 1.

In one form, the radiation head 108 is coupled to the light source 106 by way of a fiber optic cable, and is arranged and attached to a moveable member 114, such as a robotic arm. The moveable member 114 is operable to adjust the orientation and the position of the radiation head 108. Referring to FIG. 2, the radiation head 108 includes an emitter 202 and a detector 204. The emitter 202 emits or radiates the radiation beam 112 generated by the light source 106 toward a target surface 208 along the vehicle body 102. The detector 204 receives one or more reflected radiation beams 210 reflected from the vehicle body 102. The radiation head 108 is communicably coupled to the controller 110 by way of, for example, wires, and transmits data indicative of the reflected radiation beams 210 to the controller 110.

The controller 110 is a computer that includes, for example, a processor, a computer readable medium, and other electronic components. The controller 110 is further connected to one or more user interface 115, such as a keyboard and a monitor (e.g., liquid crystal display) for allowing an operator to view one or more graphical user interface configured for operating the system 100. The controller 110 is configured to control the light source 106 and the radiation head 108 for emitting the THz radiation beam 112. The controller 110 further analyzes the signals received from the radiation head 108 to determine the thickness of one or more paint layers of the target surface 208. An example of such analysis is provided in Applicant's co-pending application, U.S. Ser. No. 14/829,888, filed Aug. 19, 2015 and titled "ROBOTIC VEHICLE PAINTING INSTRUMENT INCLUDING A TERAHERTZ RADIATION DEVICE" which is commonly owned with the present application and the contents of which are incorporated herein by reference in its entirety.

To align the radiation head 108 with the target surface 208, the system 100 further includes a reference image projector 116 (FIG. 1) that projects a reference image onto the target surface 208 using one or more visible light devices. Referring to FIGS. 3A to 3D, in one form, the reference image projector 116 includes two visible light devices 302A and 302B (i.e., collectively known as light devices 302) for generating the reference image. The light devices 302 are disposed with the radiation head 108 and can be any suitable visible light device, such as a visible laser device.

The light devices 302 are configured to project different images to form the reference image. In one form, the light device 302A forms a linear pattern 304 that includes a plurality of dots arranged along two orthogonal axes, and the light device 302B form a circular pattern 306 of a plurality of rings having varying diameters and concentrically disposed with one another. In another form, the circular pattern 306 may be offset to a shallow angle such that a slight change in angle results in a large distortion of the projected pattern for a visual assessment described further below. The light devices 302 are configured to project the respective images such that the images are superimposed to form a reference image 308. The light devices 302 can be configured to form other suitable geometric shapes and/or patterns, and thus the patterns and reference image are not limited to the dots and rings illustrated herein.

Figure 4A:
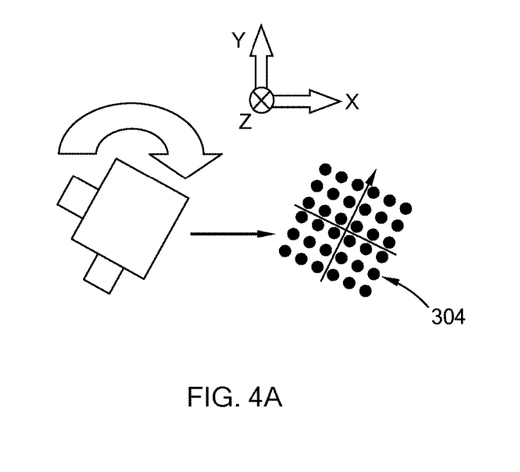
FIGS. 4A and 4B illustrate rotational relationship of the radiation head with the light patterns in accordance with the teachings of the present disclosure.
Figure 4B:
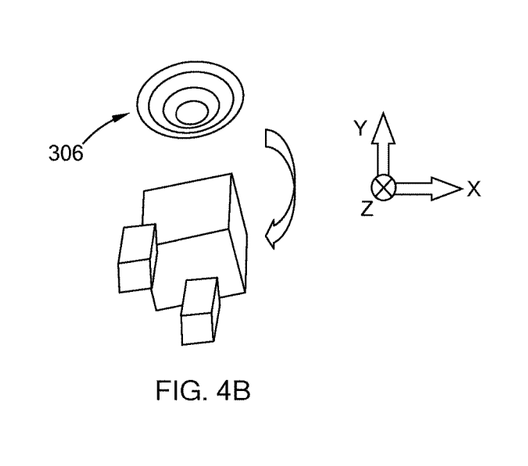

With the reference image projector 116 arranged with the radiation head 108, the position and rotation of the radiation head 108 influences one or more visual characteristics of the patterns projected by the light devices 302. For example, FIG. 4A illustrates a rotational relationship of the radiation head 108 and the linear pattern 304 about a z-axis and FIG. 4B illustrates a rotational relationship of the radiation head 108 and the circular pattern 306 about a X-Y axes. As illustrated, visual characteristics of the patterns 304 and 306 are dependent on the position of the radiation head 108, and thus, may be correlated to one or more positional characteristics of the radiation head 108 relative to the target surface 208.

Figure 3A:
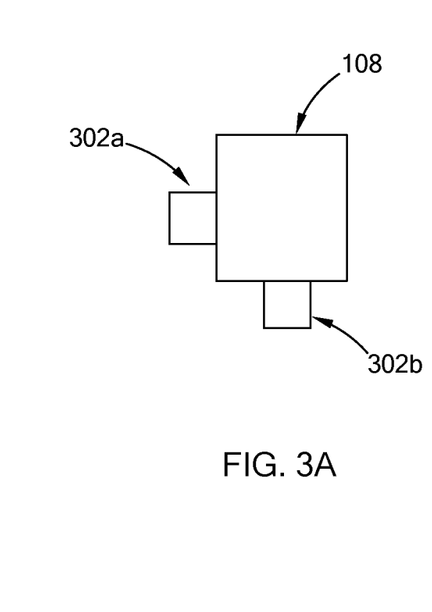
FIG. 3A illustrates light devices of the reference image projector arranged with the radiation head in accordance with the teachings of the present disclosure.
Figure 3B:
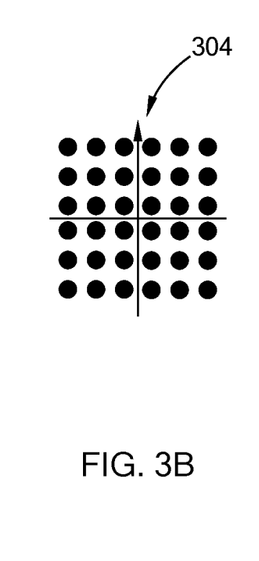
FIGS. 3B and 3C illustrate patterns formed by the light devices of FIG. 3A.
Figure 3C:
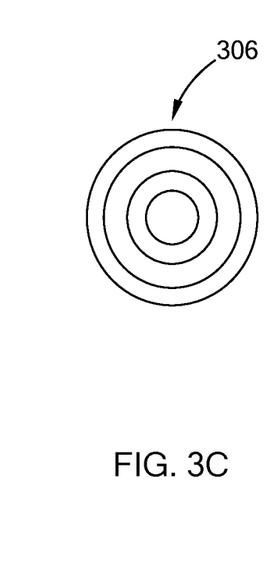
Figure 3D:
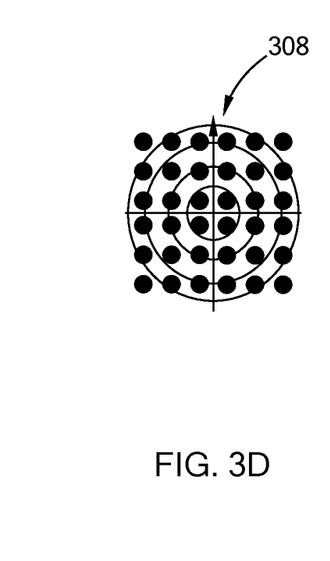
FIG. 3D illustrates a reference image formed by the patterns of FIGS. 3B and 3C.

The reference image projector 116 is arranged with the radiation head 108 such that the radiation beam 112 is surrounded by the reference image 308 and the visual characteristics of the reference image 308 is within one or more calibrated visual characteristics when the radiation head 108 is at a measurement position relative to the target surface 208 (e.g., the radiation head 108 is normal to and at a designated offset from the target surface 208). The visual characteristics include but are not limited to at least one of size, deformation, and rotational position of the reference image 308. For example, FIG. 3D illustrates the reference image 308 having calibrated visual characteristics when the radiation head 108 is at the measurement position. At the measurement position, the circular pattern 306 is positioned within the boundaries formed by the linear pattern 304, the linear pattern 304 forms a square grid made of the plurality of dots, and the circles of the circular patterns 306 are concentrically arranged with each other.

Figure 5A:
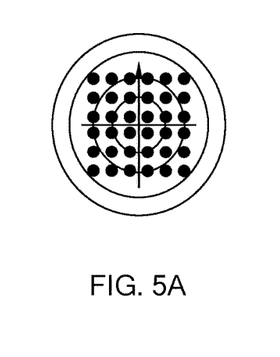
FIGS. 5A, 5B, and 5C illustrate different visual characteristics of the reference image based on a position of the radiation head in accordance with the teachings of the present disclosure.
Figure 5B:
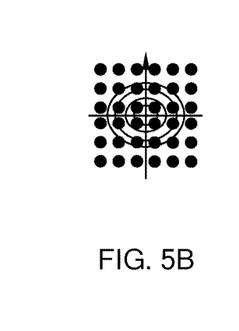
Figure 5C:
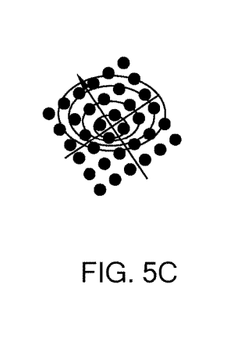

The visual characteristics of the reference image 308 indicate the positional relationship of the radiation head 108 relative to the target surface 208. Such positional relationship includes but are not limited to distance, rotational alignment, and angular alignment of the radiation head 108 relative to the target surface 208. For example, FIGS. 5A to 5C illustrate the reference image when the radiation head 108 is at positions other than the measurement position with respect to the target surface 208. In FIG. 5A, the circular pattern 306 is larger than that of FIG. 3D and correlates to a position in which the distance of the radiation head 108 is too far from the target surface 208. Conversely, in FIG. 5B, the circular pattern 306 is smaller than that of FIG. 3D and correlates to a position in which the distance of the radiation head 108 is too close to the target surface 208. In FIG. 5C, the linear pattern 304 is rotated and the circular pattern 306 is deformed which correlate to a position in which the radiation head 108 is too close to the target surface 208 and is not normal to the target surface 208. Other correlations between the visual characteristics of the reference image and various positions of the radiation head 108 are possible, and within the scope of the present disclosure.

Using the calibrated visual characteristics and predetermined correlations between the visual characteristics of the reference image and the position of the radiation head 108, a visual assessment of the reference image projected on the target surface 208 is conducted to align the radiation head 108 with the target surface 208. In one form, the visual assessment is performed by that operator that adjusts the position of the radiation head 108 by operating the moveable member 114 until the reference image projected on the target surface 208 is within the calibrated visual characteristics.

In another form, the system 100 is configured to include a visual recognition instrument that compares visual characteristics of the reference image to the calibrated visual characteristics and uses pre-stored correlations between visual characteristics and positions of the radiation head 108 to align the radiation head 108. For example, the visual recognition instrument has a camera that captures an image of the reference image and transmits the captured image to the controller 110. The controller 110 is configured to determine the position of the radiation head 108 based on the captured image of the reference image, and align the radiation head 108 by controlling the moveable member 114 until the visual characteristics of the reference image substantially match that of the calibrated visual characteristics. In yet another form, the visual assessment is performed by a combination of an operator and the controller 110. For example, the operator may make an initial adjustment of the radiation head 108 when the visual characteristics of the reference image are notably different from the calibrated visual characteristics, and then then operate the controller 110 to perform a further analysis to further tune the position of the radiation head.

In one form, the controller 110 may display, an animated representation of the moveable member 114, the radiation head 108, and the target surface 208, on the monitor. In the animated the representation, the controller 110 displays one or more indicia for indicating the position of the radiation head 108 relative to the target surface 208 based on the visual assessment of the reference image. For example, the controller 110 may show a circular bubble that is displayed in different colors and/or sizes for indicating the distance between the radiation head 108 relative to the target surface. Other indicia may be used for indicating angle measurement. Such visual indicators assist the operator in aligning the radiation head 108 with the target surface.

Figure 6:
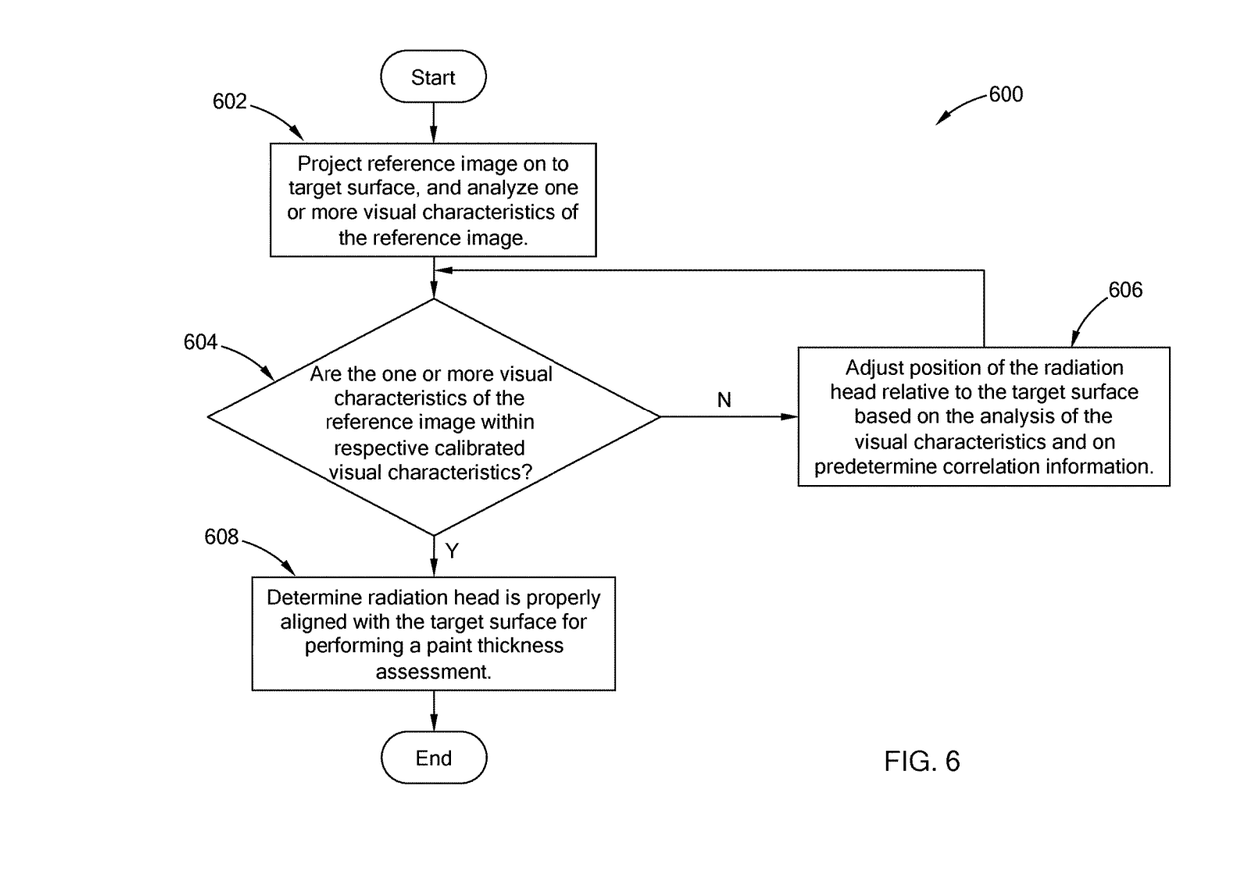
FIG. 6 is a flowchart of a radiation head alignment routine in accordance with the teachings of the present disclosure.

Referring to FIG. 6 a radiation head alignment routine 600 executed by the system 100 is provided. At 602, the system 100 projects the reference image on to the target surface, and analyzes one or more visual characteristics of the reference image. For example, the controller 110 operates the reference image projector 116 to project the reference image on the target surface. The visual characteristics of the reference image may be analyzed by the controller 110, the operator of the system 100, or a combination thereof.

At 604, a visual assessment is performed to determine whether one or more visual characteristics of the reference image are within respective calibrated visual characteristics. For example, the size, rotation, and/or deformation of the reference image being projected is compared to a calibrated size, calibrated rotation, and/or calibrated deformation.

If the one or more visual characteristics are not within respective calibrated visual characteristics, the position of the radiation head 108 is adjusted based on the analysis of the visual characteristics and on predetermined correlation information, at 606. For example, in one form, the size of the reference image correlates to a distance of the radiation head 108 relative to the target surface 208. Thus, if the size of the reference image is smaller than the calibrated size, then the radiation head 108 is too close to the target surface. From 606, the visual characteristics of the reference are again compared to the calibrated visual characteristics at 604. If the visual characteristics are within the calibrated visual characteristics, at 608, the radiation head 108 is determined to be properly aligned with the target surface 208 for performing a paint thickness assessment and the alignment routine 600 ends.

Through the use of the reference image projector, the invisible terahertz radiation beam can be visualized to accurately align the radiation head relative to the target surface by an operator and/or a controller. In the example provided herein, the reference image comprises two patterns that are superimposed with each other. By superimposing both patterns on top of each other it is possible to determine rotation and distance about three axes of the terahertz radiation head.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A system for measuring a coating thickness on a target surface, the system comprising:
   a terahertz spectroscopy device including a radiation head, the radiation head operable to project a terahertz radiation beam onto a target surface and receive a reflected beam; and
   a reference image projector including a visible light device and operable to project a reference image using the visible light device onto the target surface, wherein a visual characteristic of the reference image indicates at least one of distance, rotational alignment, and angular alignment of the radiation head relative to the target surface.

2. The system of claim 1, wherein:
   the terahertz spectroscopy device includes a terahertz light source that is operable to generate the terahertz radiation beam, and
   the radiation head includes an emitter to emit the terahertz radiation beam and a detector for receiving the reflected beams.

3. The system of claim 1, wherein the visible light device is positioned with the radiation head.

4. The system of claim 1 further comprising a controller configured to control the position and orientation of the radiation head with respect to the target surface based on the visual characteristic of the reference image.

5. The system of claim 1, wherein the reference image comprises at least two patterns that are superimposed with each other, each pattern has a visual characteristic that is dependent on the position of the radiation head with respect to the target surface, and is independent of the other patterns.

6. The system of claim 5, wherein one pattern of the at least two patterns is a plurality of dots arranged in a matrix form and another pattern of the at least two patterns is multiple rings having different diameters and concentrically positioned with one another.

7. The system of claim 5, wherein the at least two patterns are different geometric shapes that are superimposed with each other.

8. The system of claim 1, wherein the visual characteristic of the reference image includes at least one of size, deformation, and rotational position.

9. A method for aligning a terahertz radiation head of a spectroscopy device with a target surface, the method comprising:
   projecting, by a visible light source, a reference image onto the target surface, wherein a terahertz radiation beam emitted from the terahertz radiation head is surrounded by the reference image;
   analyzing a visual characteristic of the reference image to determine the alignment of the terahertz radiation head with respect to the target surface, wherein the visual characteristic of the reference image is indicative of at least one of distance, angle, and rotational orientation of the terahertz radiation head; and
   aligning the terahertz radiation head with the target surface such that the visual characteristic of the reference image is within a calibrated visual characteristic.

10. The method of claim 9, wherein the calibrated visual characteristic is representative of the reference image when an alignment of the terahertz radiation head with respect to the target surface is optimal for receiving a reflected terahertz radiation beam from the target surface.

11. The method of claim 9, wherein the projecting the reference image further comprises projecting at least two patterns that are superimposed with each other on the target surface to form the reference image.

12. The method of claim 11, wherein one pattern of the at least two patterns is a plurality of dots arranged in a matrix form and another pattern of the at least two patterns are multiple rings having different diameters and concentrically positioned with one another.

13. The method of claim 11, wherein the at least two patterns are different geometric shapes that are superimposed with each other.

14. The method of claim 9, wherein the visual characteristic of the reference image includes at least one of a size, a deformation, and a rotational position.

15. An alignment method for a terahertz radiation head of a spectroscopy device with a target surface of a vehicle, the method comprising:
   projecting an image onto the target surface using a visible light source; and
   aligning the terahertz radiation head with the target surface until a visual characteristic of the image meets a calibrated characteristic, wherein the calibrated characteristic is representative of the image when the terahertz radiation head is at a calibrated position.

16. The method of claim 15, wherein the projecting the image further comprises projecting two patterns that are superimposed with each other on the target surface to form the reference image, wherein each pattern has a visual characteristic that is dependent on the position of the terahertz radiation head with respect to the target surface, and is independent of the other pattern.

17. The method of claim 16, wherein one pattern of the two patterns is a plurality of dots arranged in a matrix form and the other pattern of the two patterns are multiple rings having different diameters and concentrically positioned with one another.

18. The method of claim 16, wherein the two patterns are different geometric shapes that are superimposed with each other.

19. The method of claim 15, wherein the visual characteristic of the image includes at least one of a size, a deformation, and a rotational position of the image.

20. The method of claim 15, wherein the visual characteristic of the image is indicative of at least one of distance, angle, and rotational orientation of the terahertz radiation head.

* * * * *